United States Patent [19]

Igaue et al.

[11] Patent Number: 5,304,160
[45] Date of Patent: Apr. 19, 1994

[54] DISPOSABLE DIAPERS

[75] Inventors: Takamitsu Igaue; Hiroyuki Tanji, both of Kawanoe, Japan

[73] Assignee: Uni-Charm Corporation, Ehime, Japan

[21] Appl. No.: 20,357

[22] Filed: Feb. 22, 1993

Related U.S. Application Data

[63] Continuation of Ser. No. 863,019, Apr. 3, 1992, abandoned.

[30] Foreign Application Priority Data

Apr. 10, 1991 [JP] Japan .................. 3-032167

[51] Int. Cl.⁵ .............................................. A61F 13/18
[52] U.S. Cl. ............................ 604/385.2; 604/358; 604/385.1
[58] Field of Search ............ 604/385.1, 385.2, 358, 604/381, 382, 384, 386, 387, 397, 398

[56] References Cited

U.S. PATENT DOCUMENTS 3,658,063  4/1972  Schaar .
4,804,379  2/1989  Toth et al. .
4,900,384  2/1990  Sanders et al. .
4,990,147  2/1991  Freeland .
5,037,416  8/1991  Allen et al. .
5,069,678  12/1991 Yamamoto et al. .
5,087,258  2/1992  Sims .

FOREIGN PATENT DOCUMENTS

45217/85    2/1986   Australia .
0376022     7/1990   European Pat. Off. .
0421473     4/1991   European Pat. Off. .
49-120439  10/1974   Japan .
2216393    10/1989   United Kingdom .

Primary Examiner—Randall L. Green
Assistant Examiner—Karin M. Reichle
Attorney, Agent, or Firm—Fred Philpitt

[57] ABSTRACT

A second topsheet formed with an opening is bonded along its outer periphery to a topsheet of a disposable diaper and there are provided a pair of flaps having inner side edges wrapping therein elastic members, respectively, and outer side portions bonded to an underside of the second topsheet at both sides of the opening 16 so that the pair of flaps 17 define a second opening 18 serving to receive excretion.

1 Claim, 4 Drawing Sheets

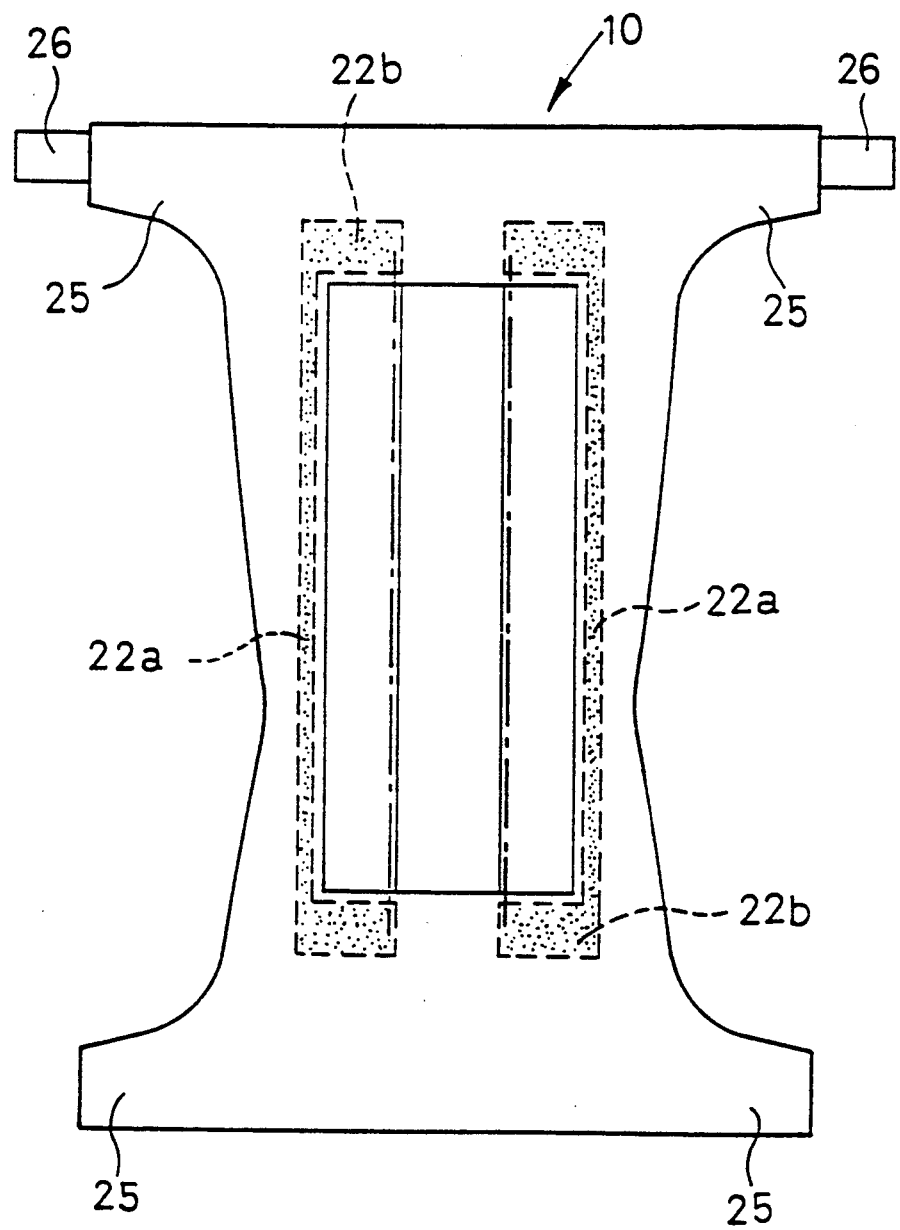

DISPOSABLE DIAPERS

This is a continuation of application Ser. No. 07/863,019, filed Apr. 3, 1992, and now abandoned, and the benefits of 35 USC 120 are claimed relative to it.

BACKGROUND OF THE INVENTION

This invention relates to disposable diapers to absorb and hold excretion.

Japanese Patent Application Disclosure Gazette No. 1986-41304 discloses a disposable diaper in which the portion of a topsheet corresponding to a crotch area is cut away to form a longitudinal opening serving to receive excretion, and elastic members are attached, but not in a wrapped manner, to the underside of the topsheet at locations slightly spaced outward from opposite side edges of an the opening defined by opposite inner side edges of the topsheet.

In the above-mentioned disposable diaper of the prior art, the elastic members are attached, but not in a wrapped manner, i.e. in exposed manner, to the underside of the topsheet at the locations slightly spaced outward from the respective inner side edges of the topsheet defining the opposite side edges of the opening, probably because it is practically difficult for the conventional equipment for high speed mass-production of disposable diapers to bond the elastic members with adhesive onto the inner side edges of the topsheet in a neat order and, even when such bonding is attempted, adhesive will partially swell out inwardly and be unpleasantly in contact with the wearer's skin. While such swelling out of adhesive could be avoided by wrapping the elastic members with the inner side edges of the topsheet, such wrapping of the elastic members will require further processing of the inner side edges which define the side edges of the opening and, even after such processing has been done, it will be difficult for the conventional equipment to achieve rapid bonding and wrapping of the elastic members along the inner side edges thus further processed.

It should be noted here that, so far as the elastic members are attached to the topsheet at the locations spaced outward from the inner side edges of the topsheet and not wrapped by these inner side edges, these inner side edges can never form fine gathers. In view of the fact that these inner side edges should be in contact with the wearer's skin and form effective seals, the desired effect of preventing excretion, particularly fluid excretion from leaking, will be seriously affected by the absence of the fine gathers.

Accordingly, it is a principal object of the invention to provide disposable diapers allowing said problem to be eliminated by providing a pair of separately formed stretchable flaps on both sides of the opening formed in the inner topsheet.

SUMMARY OF THE INVENTION

A disposable diaper according to the invention comprises an integral laminate of a liquid-permeable first topsheet, a liquid-impermeable backsheet, a liquid-absorbent core sandwiched between the first topsheet and the backsheet and a liquid-resistant second topsheet overlying the first topsheet, wherein the second topsheet is formed substantially at its central area with a first opening having a longitudinal dimension larger than a transverse dimension and bonded along its outer periphery onto the first topsheet, and wherein there are provided adjacent opposite side edges of the first opening extending longitudinally thereof elastic members being stretchable longitudinally of the first opening, the improvement comprising:

that there are provided on both sides of the first opening a pair of flaps which extend inwardly above the core from undersides of respective side portions of the second topsheet so that opposite inner side edges define a second opening therebetween, longitudinally opposite ends of the respective flaps extend under the second topsheet, the inner side edges of these flaps wrap the elastic members, and outer side portions of these flaps are bonded to the underside of the second topsheet overlying the respective flaps.

Preferably the outer side portions of said flaps are bonded with adhesive to the undersides of the second topsheet portions overlying the outer side portions so as to leave the respective inner side edges of the first opening free.

During use of the diaper constructed as mentioned above in accordance with the teachings of the invention, the opposite inner side portions of the second topsheet are lifted under contraction of the respective elastic members out from the first topsheet and form fine gathers tightly fitting the wearer's skin so that excretion flows through the second opening defined by said inner side edges of the second topsheet into the pockets formed between the first and second topsheets and is held within the diaper.

The diaper of the invention has a unique construction such that there are provided a pair of flaps separate from of the second topsheet, the inner side edges of which define the opposite side edges of the second opening. The elastic members are wrapped with the inner side edges, respectively, to provide these inner side edges with elastic stretchability. The outer side portions of the respective flaps are bonded to the underside of the second topsheet at opposite side portions thereof. Such construction allows the elastic members to be attached to the desired locations such as the inner side edges of the opening without swelling out or exposure of adhesive, on the one hand, and allows fine gathers to be formed in the inner side edges of the respective flaps, on the other hand. Such gathers allow the inner side edges of the respective flaps to fit the wearer's skin to provide a damming effect against an excretion leak.

Another feature of the invention is that the outer side portions of the respective flaps are bonded with adhesive to the underside of the second topsheet at the portions thereof overlying the outer side portions, respectively, leaving the inner side edges of the second topsheet portions free. Such construction allows excretion which flows over the inner side edges of the flaps to be held back by the groove-like pockets defined between the inner side edges of the first opening defined by the topsheet and the flaps and thereby prevents flow further outward.

These and other features and advantages of the invention will be better understood from the following description made to reference with the accompanying drawings.

BRIEF DESCRIPTION OF THE DRAWINGS

FIG. 4 is a plan view showing the inner side of the diaper as unfolded.

PREFERRED EMBODIMENTS OF THE INVENTION

Figure 1:
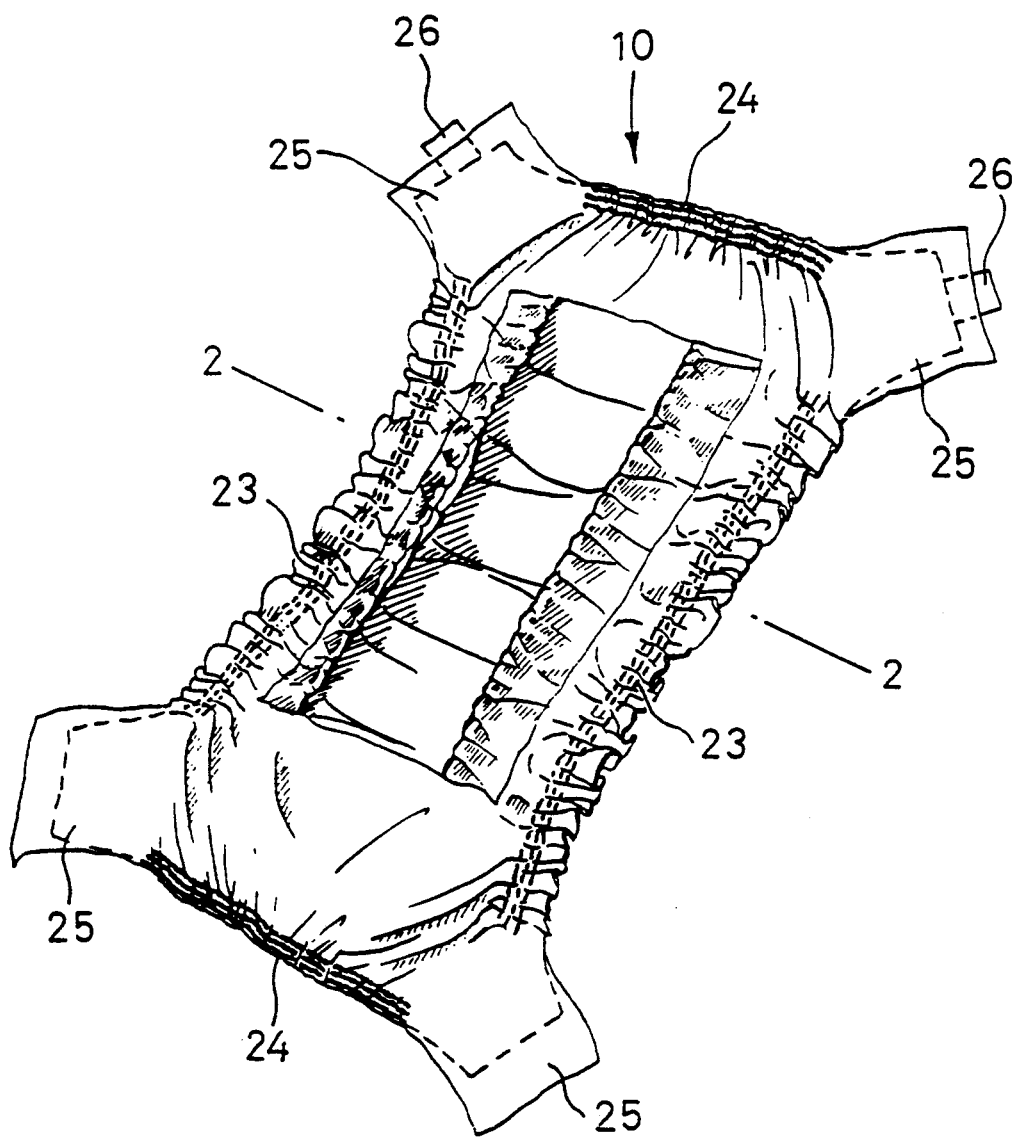
FIG. 1 is an isometric view exemplarily showing a disposable diaper constructed according to the invention as viewed from its inner side.
Figure 2:
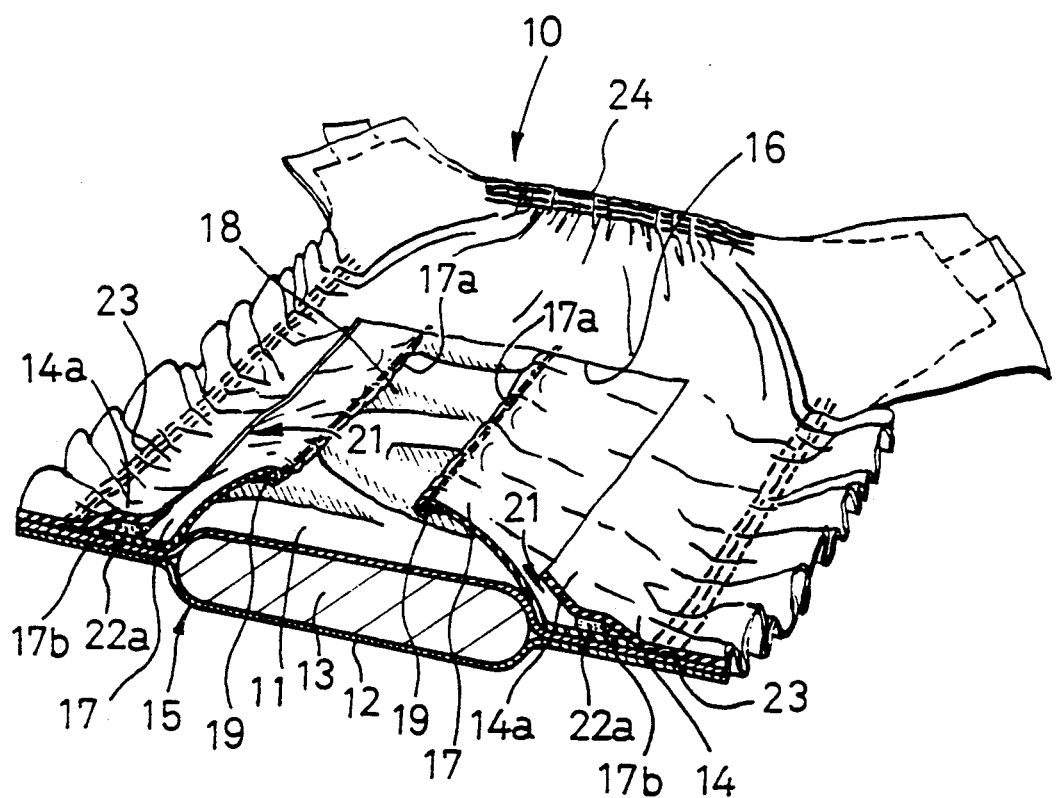
FIG. 2 is an isometric view partially in section taken along a line 2—2 in FIG. 1.
Figure 3:
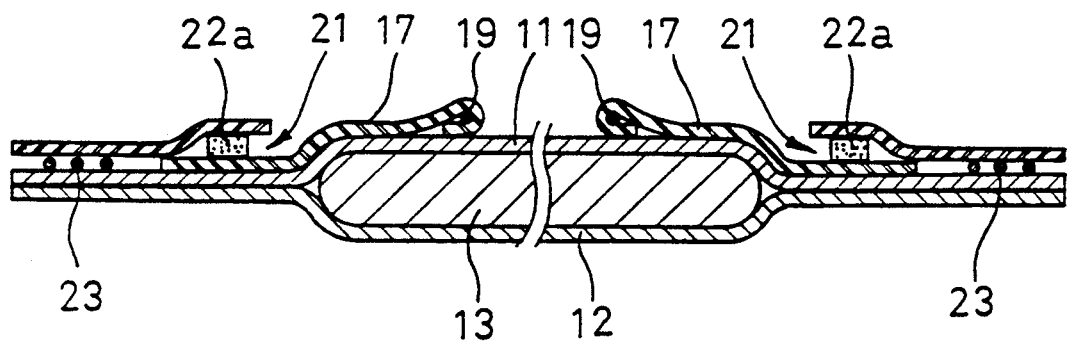
FIG. 3 is a sectional view taken along a line 2—2 in FIG. 1.

As shown in FIGS. 1 through 3, a diaper 10 comprises a laminate 15 which comprises, in turn, a liquid-permeable first topsheet 11, a liquid-impermeable backsheet 12, a liquid-absorbent core 13 sandwiched between these sheets and liquid-resistant second topsheet 14 overlying the first topsheet 11. The second topsheet 14 is formed centrally with a first opening 16 having a longitudinal dimension larger than the transverse dimension. The opening 16 may be positioned to occupy at least the crotch area.

A pair of relatively narrow liquid-resistant flaps 17 extend inwardly above the core 13 from undersides of respective side portions 14a of the second topsheet 14 so that opposite inner side edges 17a of the respective flaps 17 define a second opening 18 therebetween. Longitudinally opposite ends of the respective flaps 17 extend under the second topsheet 14. The inner side edge 17a of each flap 17 is provided with a longitudinally stretchable elastic member 19 bonded thereto with adhesive and wrapped therein. An outer end portion 17b of each flap 17 is bonded to the side portion 14a of the second topsheet 14 overlying the outer end portion 17b with a line of adhesive 22a leaving the inner side edge of the second topsheet 14 or the first opening 16 free so that a groove-like pocket 21 is defined between each inner side edge of the first opening 16 formed by the first topsheet 11 and the associated flap 17. Longitudinally opposite ends of each flap 17 are bonded to the second topsheet 14 with adhesive 22b (See FIG. 4).

There are provided between portions of the first topsheet 11 and the backsheet 12 extending outward from each side of the core 13, on one side, and the associated side portion 14a of the second topsheet 14 a plurality of elastic members 23 which are longitudinally stretchable so as to fit around each leg of the wearer. Similarly, longitudinally opposite ends are provided, between said sheets 11, 12 and said sheet 14, with a plurality of elastic members 24 which are transversely stretchable so as to fit around the wearer's waist.

The first topsheet 11 may be made of nonwoven fabric, porous plastic film or the like. The backsheet 12 may be made of plastic film, a laminate sheet consisting of this plastic film and nonwoven fabric, or the like. The core 13 may be made of fluff pulp mixed with superabsorbent polymer powder, or the like. The second topsheet and the respective flaps 17 are preferably made of liquid-impermeable but air-permeable nonwoven fabric. The expression "liquid-resistant" used herein should be understood as the second topsheet has water repellency sufficient to prevent fluid excretion from readily permeating this second topsheet of the diaper during use thereof.

As will be apparent from FIG. 1, the diaper 10 has wings 25 extending outward from opposite ends of front and rear waist lines and tape fasteners 26 are attached to the wings 25 of the rear waist line so that free ends of these tape fasteners 26 may be temporarily bonded to the backsheet 12 on the front section of the diaper to put the diaper on the wearer.

What is claimed is:

1. A disposable diaper comprising an integral laminate of
    (a) a liquid-permeable first topsheet (11) having opposite longitudinal side portions, a liquid impermeable backsheet (12), and a liquid absorbent core (13) sandwiched between said first topsheet (11) and said backsheet (12),
    (b) a second topsheet (14)
        (1) consisting of a single sheet of material,
        (2) having a surface area which is substantially coextensive with the surface area of said first topsheet (11) except for a centrally located first opening (16) formed entirely within the outer periphery of said second topsheet (14), said first opening (16) having two spaced apart lateral sides and two spaced apart end sides, and
        (3) being bonded adjacent its outer periphery to the periphery of said first topsheet (11),
    (c) elastic members (23) provided between said opposite longitudinal side portions of said first topsheet (11) and said second topsheet (14), said elastic members (23) being stretchable longitudinally,
    (d) a pair of spaced apart flaps (17) having opposite inner side edges (17a), and opposite outer side portions (17b) and extending partially into said first opening (16), said pair of flaps (17) extending inwardly from the undersides of said spaced apart lateral sides of said first opening (16), respectively so that said opposite inner side edges (17a) of said pair of flaps (17) define between them a second opening (18), longitudinally opposite ends of each of said pair of flaps (17) extending under said spaced apart end sides of said second topsheet (14), respectively said outer side portions (17b) of said pair of flaps (17) being bonded to the underside of said second topsheet (14), and
    (e) elastic members (19) encased in said opposite inner side edges (17a), respectively along lines which are adjacent to and generally parallel to said two spaced apart lateral sides of said first opening (16), said elastic members (19) being stretchable longitudinally.

* * * * *